United States Patent [19]

Lee

[11] Patent Number: 4,487,968

[45] Date of Patent: Dec. 11, 1984

[54] PRODUCTION OF TERTIARY HALOALKYLPHOSPHINE OXIDES

[75] Inventor: Fui-Tseng H. Lee, Princeton, N.J.

[73] Assignee: FMC Corporation, Philadelphia, Pa.

[21] Appl. No.: 392,901

[22] Filed: Jun. 28, 1982

[51] Int. Cl.$^3$ ............................................... C07F 9/53
[52] U.S. Cl. ...................................................... 568/14
[58] Field of Search .................................... 568/14, 15

[56] References Cited

U.S. PATENT DOCUMENTS

| | | | |
|---|---|---|---|
| 3,306,937 | 2/1967 | Clampitt et al. | 260/606.5 |
| 3,716,580 | 2/1973 | Maier | 260/488 J |
| 3,931,333 | 1/1976 | Neumaier et al. | 260/606.5 P |
| 3,998,886 | 12/1976 | Lippsmeier et al. | 260/606.5 P |
| 4,124,456 | 11/1978 | Yagupolsky et al. | 568/14 X |
| 4,287,119 | 9/1981 | Braksmayer et al. | 568/14 X |
| 4,346,236 | 8/1982 | Lee | 568/15 |

OTHER PUBLICATIONS

CA 55, 11302c, (1961).
CA 70, 115259d, (1969).
CA 72, 121634e, (1970).
CA 74, 31815b, (1971).
CA 83, 28369q, (1975).
CA 77, 101894q, (1972),
CA 64, 6681h, (1966).
CA 68, 13084j, (1968).
CA 69, 87089g, (1968).
CA 77, 101894q, (1972).
CA 80, 15066b, (1974).

*Primary Examiner*—Helen M. S. Sneed
*Attorney, Agent, or Firm*—Robert D. Jackson; Eugene G. Horsky; Eugene G. Seems

[57] ABSTRACT

A process of preparing a tertiary haloalkylphosphine oxide by reacting a tertiary hydroxyalkyl phosphine with hydrogen halide under acidic conditions is described.

10 Claims, No Drawings

PRODUCTION OF TERTIARY HALOALKYLPHOSPHINE OXIDES

This invention relates to tertiary haloalkylphosphine oxides, particularly to a method of producing them from tertiary hydroxyalkyl phosphines.

Tertiary haloalkylphosphine oxides constitute a known and valuable class of chemical entities. For instance, these compounds are useful as pesticides, chemical intermediates, additives for fuels and lubricants and flameproofing agents, particularly in connection with the development of flame retardant polymers and plastic compositions.

Several methods of synthesizing tertiary haloalkylphosphine oxides are available. A brief survey of the chemical reactions involved together with prior art citations are given below.

a. From Hydroxyalkylphosphine Oxides

Thionyl Chloride

K. A. Petrov et al., Zh. Obshch. Khim. 31, 3411-14 (1961)—CA 57, 4693c;
K. A. Petrov et al., Zh. Obshch. Khim. 35 (11), 2062-5 (1965)—CA 64, 6681h;
E. B. Trostyanskaya et al., Zh. Obshch. Khim. 37 (7), 1655-7 (1967)—CA 68, 13084j;
L. Maier, Angew. Chem. Int. Ed. Engl. 1968, 7 (5), 385—CA 69, 19265m;
D. C. Smith et al., J. Med. Chem. 1968, 11(5), 1060-3—CA 69, 87089g;
K. Morita et al., CA 73, 66728g.

Phosgene

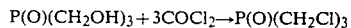

Kleiner, H., Ger. Offen. No. 2,060,217—CA 77, 101894q;
M. Reuter et al., Ger. Offen. No. 2,219,173—CA 80, 15066b;
Kleiner, H., J. Am. Chem. 1974, (5), 751-64—CA 81, 91643y.

Oxalyl Chloride

n=1,2; R=alkyl; X=Br, Cl
Kleiner, H., Ger. Offen. No. 2,060,217—CA 77, 101894q;
M. Reuter et al., Ger. Offen. No. 2,219,173—CA 80, 15066b;
Kleiner, H., J. Am. Chem. 1974, (5), 751-64—CA 81, 91643y.

Phosphorus Pentachloride

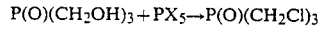

X=Br, Cl
M. Reuter et al., Ger. Pat. No. 1,064,511; CA 55, 11302c;
L. Maier et al., Helv. Chem. Acta. 1969, 52(3), 858-7-1—CA 70, 115259d;
E. N. Tsvekov et al., Zh. Obshch. Khim. 1979, 40(2), 285-91—CA 72, 121634e;
L. Maier, Helv. Chem. Acta. 1970, 53(8), 2069-70—CA 74, 31815b;
L. Maier, Ger. Offen. No. 1,963,068—CA 73, 66728g.

Hydrogen Halide

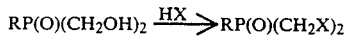

X=Br, Cl
Frank, A. W., Phosphorus Sulfur 1978, 5(2), 197-9—CA 90, 137064b;
H. Newmaier, Ger. Offen. No. 2,347,109—CA 83, 28369q;

b. From Phosphorus Halides

Formaldehyde

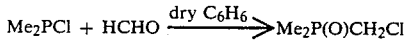

V. M. Zimin et al., Russian Patent Application No. 1,938,098, June 21, 1973—CA 81, 105628m.

Grignard Reagent

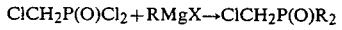

J. P. King, Inorg. Chem. 4(2), 198-202 (1965)—CA 62, 6120c;
L. Maier, Angew. Chem. Int. Ed. Engl. 1968, 7(5), 385—CA 69, 19265m;
L. Maier et al., Helv. Chem. Acta. 1969, 52(3), 845-5-7—CA 70, 115258c;
L. Maier et al., Helv. Chem. Acta. 1971, 54(6), 1651-60—CA 75, 151876q;
Y. A. Levin et al., Zh. Obshch. Khim. 1972, 42(5), 1166-7—CA 77, 101894q.

Dihaloalkane

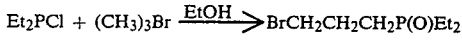

G. Tsiarinin et al., Zh. Obshch. Khim. 36(8), 1430-3 (1966)—CA 66, 11007t.

c. From Phosphonium Salts and Alkali

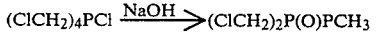

M. I. Kabachnik et al., U.S.S.R. Pat. No. 170,972—CA 63, 9991e;
K. A. Petrov et al., Usp. Khim. 1968, 37(7), 1218-42—CA 70, 20112m.

d. Michaelis—Arbuzov Reaction

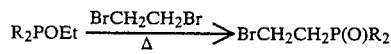

R. F. Struck et al., J. Med. Chem. 9(3), 414-16 (1966)—CA 65, 2290f;
O. Dahl., J. Chem. Soc., Perkin Trans. 1 1978, (9) 947-54—CA 91, 39579g.

Although generally satisfactory for laboratory or pilot plant preparations, the reactions aforesaid do not lend themselves to the actual manufacture of haloalkylphosphine oxides as well as might be desired. Reactions in category a., for example, require as starting materials hydroxyalkyl phosphine oxides. In a commercial situation, these would normally be produced on the plant premises by oxidation of the corresponding precursor phosphine with hydrogen peroxide. However, since the reaction is exothermic, some means of cooling the reactor vessels would be needed. This is objectionable in that it increases both capital investment and operational overhead of a chemical plant. Furthermore, high strength hydrogen peroxide required to effect oxidation of the intermediate hydroxyalkyl phosphine, is a relatively high cost oxidant. An improved process of preparing the tertiary hydroxyalkyl phosphine oxide intermediate, that eliminates the need for using hydrogen peroxide is disclosed in my copending application Ser. No. 232,770, filed on Feb. 9, 1981, U.S. Pat. No. 4,346,236. In the process of the application, water soluble tris-alkyl phosphine oxides are prepared by heating the precursor phosphines in an acidic aqueous solution.

So far as the other reaction types aforesaid are concerned, these tend to be impractical for commercial purposes. Certainly Grignard reagents (category b.), which require ether as a solvent would be too hazardous for use in large scale production. Nor have the other reaction categories summarized above been found suitable or been developed for manufacturing haloalkylphosphine oxides. Manifestly, there is a need for more economically effective methods by which these valuable flame retardant compounds can be realized.

In accordance with the present invention, there is provided a simple one-step process of producing tertiary haloalkylphosphine oxides comprising reacting, under acidic conditions, a tertiary phosphine having at least one hydroxyalkyl group attached to the phosphorus atom, with a hydrogen halide selected from the class consisting of hydrogen chloride and hydrogen bromide, whereby the hydroxy group is replaced with halide from the said hydrogen halide to form the corresponding tertiary haloalkylphosphine and concomitant elimination of water which under the said acidic conditions reacts with the tertiary haloalkylphosphine to give the tertiary haloalkylphosphine oxide aforesaid. The chemistry of the process can be represented by the following scheme:

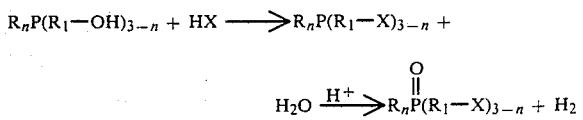

wherein X is chlorine or bromine; R is a hydrocarbon radical, $R_1$ is an alkylene radical and n is 0, 1 or 2.

As will be observed, for every molecular equivalent of OH replaced by halogen, there is formed a corresponding equivalent of water which is the source of oxygen in the phosphine oxide end product. When more than one hydroxyalkyl group is present in the phosphine, however, an excess of water is eliminated. Such extraneous water is desirably removed, preferably by azeotropic distillation. This is conveniently effected by conducting the reaction in the presence of a water-immiscible organic solvent and distilling off the solvent/water azeotrope. Suitable solvents are the normally liquid, water-immiscible aromatic hydrocarbons such as benzene, toluene and xylene. Although the extent of halogenation is indicated by the quantity of water evolved, it is not a measure of the degree of oxidation. Therefore, an assay procedure was developed whereby the course of the oxidation could be followed. In this procedure, a sample of the reaction mixture is withdrawn and treated with excess hydrogen peroxide (3%) which converts any unreacted phosphine to the oxide. The percentage of oxidation that has occurred is determined by back titrating the remaining peroxide with a standardized ceric sulfate solution. After analysis shows the oxidation to be completed, the solvent and excess water is distilled off leaving a residue of substantially pure tertiary haloalkylphosphine oxide as established by instrumental—NMR and mass spectrum—and elemental analyses.

The process of the invention should be carried out at elevated temperatures, normally no lower than about 100° C., particularly when distilling off the water/solvent azeotrope.

A generally satisfactory temperature is about 120° C. at atmospheric pressure; higher temperatures, about 150° C. to about 180° C. can be employed but may require superatmospheric pressures.

Only a small quantity of acid is needed to provide the acidic conditions for the oxidation since the function of the acid is believed to be catalytic in nature. Sulfuric acid is satisfactory although the hydrogen halide itself serves as a convenient source of acid.

So far as can be ascertained, the herein one-step process of producing tertiary haloalkylphosphine oxides by the simultaneous halogenation and oxidation of a tertiary hydroxyalkyl phosphine with hydrogen halide is of general scope and applicability. It is a mild, non-exothermic oxidative halogenation which appears to give only the fully oxidized product; at least no phosphite or phosphinate was detected. The process moreover enables oxidation and halogenation to occur in the same reaction vessel, requires no separation of intermediates and employs no expensive oxidant. It is a potentially cheaper process than the conventional two-stage processes, for example, oxidation followed by halogenation. Nevertheless, as with any organic reaction, even well established synthetic procedures, the expected or normal product may not always be obtained. The use of excessively substituted or sterically hindered reactants, as organic chemists are well aware, sometimes results in unpredictable behavior; certain classes of substituents, for example, highly electronegative or electropositive groups may cause atypical reactions. Therefore, when the statement is made that the herein invention provides a general method of producing tertiary haloalkylphosphine oxides, it is within the context of the limitations aforesaid.

Exemplary tertiary alkyl phosphines which have been found to react or can be expected to react in accordance with the process of the invention to give tertiary haloalkylphosphine oxides include the following:

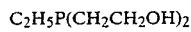

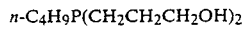

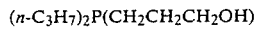

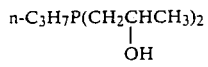

PhP(CH$_2$CH$_2$CH$_2$OH)$_2$ s-C$_4$H$_9$P(CH$_2$CH$_2$CH$_2$OH)$_2$

ClCH$_2$CH$_2$P(CH$_2$CH$_2$CH$_2$OH)$_2$

P(CH$_2$CH$_2$CH$_2$OH)$_3$

C$_4$H$_9$OC$_2$H$_5$P(CH$_2$CH$_2$CH$_2$OH)$_2$ (C$_2$H$_5$)$_2$PCH$_2$CH$_2$CH$_2$CH$_2$OH

PhPCH$_2$CH$_2$CHCH$_2$
       |
       OH

C$_6$H$_{11}$P(CH$_2$CH$_2$CH$_2$OH)$_2$

Where there is more than one hydroxyalkyl group present in the tertiary phosphine, mixed tertiary halohydroxyalkylphosphine oxides can be obtained. Such products can be illustrated by the following formulae:

$$(HOCH_2CH_2CH_2)_nP(\!\!-\!\!CH_2CH_2CH_2X)_{3-n}$$
$$\|$$
$$O$$

where n is 1 to 2;

$$n\text{-}C_4H_9\underset{\underset{CH_2CH_2CH_2X}{|}}{\overset{\overset{O}{\|}}{P}}\!-\!CH_2CH_2CH_2OH$$

Reference is now made to the following non-limiting examples.

EXAMPLE I

This example describes the unexpected result obtained by treating tris(3-hydroxypropyl)phosphine (THPP) with HCl gas.

In a small flask, THPP (20.8 grams, 0.1 mol) was placed. While stirring a slow stream of HCl gas was bubbled into near the bottom of the flask for twelve hours. The temperature of the pot mixture was maintained at 110° C.–115° C. throughout this period. The crude product was purged with nitrogen gas to remove excess HCl. The product appeared as clear viscous liquid with no apparent phosphine smell. Analysis by titration with Ce$_2$(SO$_4$)$_3$ solution after an aliquot was reacted, with excess dilute hydrogen peroxide showed that the product contained approximately 17% of the unreacted phosphine. This same titration method showed the starting material was 87% pure. Both NMR and mass spectrum analyses showed THPP and THPPO as the minor components and chlorinated THPPO as the major component. Elemental analyses showed this oxidative chlorination product contained 35.24% chlorine (% Cl Calculated for TCPPO=38.07).

EXAMPLE II

This example illustrates a scale-up run under similar conditions. A small amount of H$_2$O$_2$ was used at the end of chlorination to oxidize remaining phosphine.

In a 250 ml 3-necked flask, THPP (151 grams, 0.67 mol) was placed. The flask was equipped with an air stirrer, a HCl/N$_2$ inlet and a distilling receiver Dean Stark which is attached to a water condenser connected through an air trap to an alkali trap. The reaction flask is connected to an HCl tank through an air trap and a flow meter. A nitrogen line was connected between the HCl flow meter and the air trap to maintain a positive pressure for the entire system to prevent back-up.

Heating was gradually applied to THPP while the HCl gas bubbled through. The flow of HCl was controlled throughout the reaction so that no large excess was being trapped in the alkaline solution. Initial HCl uptake was rapid and decreased significantly after the first few hours. The heating was maintained between 97–116 to facilitate the removal of water as a by-product. The removal of water, however, should not be so rapid that there would be an insufficient amount to effect oxidation. After 27 hours, the reaction mixture was purged with N$_2$ to remove the excess HCl. The crude product which was shown to contain a small amount of unoxidized phosphine was mixed with about 200 ml of isopropanol and reacted with 19 grams of 30% H$_2$O$_2$ to insure complete oxidation. The isopropanol solution was filtered to remove a small amount of solid matter, then was evaporated under vacuum. The chlorinated product appeared as a moderately thick liquid and was analyzed. Found: %Cl (total)=31.03, %Cl (ionic)=0.24, OH number=80, % Phosphine content=0.

EXAMPLE III

This example illustrates the oxidative chlorination process applied to sec-butyl bis(3-hydroxypropyl)phosphine (BHPP). Toluene was added as solvent to facilitate the removal of water as a by-product. In addition, a trace amount of conc. H$_2$SO$_4$ was used to facilitate chlorination.

In a similar set up as described in Example II, a mixture containing 148 grams (0.67 mol) of sec-butyl bis(3-hydroxypropyl)phosphine, 150 ml of toluene and 3 drops of conc. H$_2$SO$_4$ was reacted with gaseous HCl for several hours at refluxing temperature. The progress of the reaction as indicated by the amount of H$_2$O being formed is shown in Table I. At the end of the reaction, the mixture was purged with nitrogen gas overnight to remove unreached HCl. It was distilled to remove toluene and the liquid residue dissolved in methanol/isopropanol. The alcohol solution was then mixed with 80 grams of Na$_2$CO$_2$ at room temperature for several hours, then allowed to remain for several days before it was filtered. The filtrate was reacted with a few grams of 30% H$_2$O$_2$ solution to insure complete oxidation. Excess solvent was removed and the product was analyzed. Found: %Cl (ionic)=0.25, %Cl (total)=24.82 (theoretical %Cl based on BHPP being 100% pure=27.41), OH number=20 and none of the phosphine could be detected.

EXAMPLE IV

This example describes the preparation of partially chlorinated phosphine oxides.

In a similar set up as in Example II, 143 g (0.70 mol) of THPP in 150 ml toluene was reacted with excess HCl gas at pot temperature of 100° C. for 7.5 hours. The amount of HCl gas passed through THPP/toluene during this time period was measured to be 171 grams or 4.6 moles. The amount of water collected was 11.0 ml indicating about 30% of the hydroxy groups have reacted. After toluene was distilled off, the crude product was mixed in CH₂Cl₂/isopropanol and treated with 80 grams of Na₂CO₃ powder. Then to the neutralized solution, 15.0 g of 30% H₂O₂ was added to oxidize the remaining phosphine. The solution gave a positive test to Merck peroxide test strip indicating the presence of excess peroxide and the absence of phosphine components. Excess solvent was removed and the product weighed 140 grams and appeared as moderately viscous yellow brown liquid. It was analyzed and found to have a total chlorine content of 15.12%, of which 5.52% was ionic.

EXAMPLE V

This example illustrates the preparation of tris(3-chloropropyl)phosphine oxide (TCPPO) under pressure. The conversion of tris(3-hydroxypropyl)phosphine to TCPPO appeared to proceed at a significantly faster rate as compared with that carried out under normal pressure.

In a 500 ml glass-lined reactor, THPP (52 grams, 0.25 mol) and HCl gas were charged until pressure reached 460 psi. The reactor was rocked and heated at 100° C.-120° C. for 6 hours. At the end of this period, the reactor was cooled to room temperature and the excess HCl vented into water. The reactor was opened up and more HCl vented off. A small aliquot was withdrawn from the reactor and after it was neutralized with NaHCO₃, it was analyzed for its total Cl content. It was found to contain 40.80% of chlorine indicating the chlorination was complete. The reactor was resealed and heated to 140° C.-150° C. for five hours. The maximum pressure build-up during this period was 295 psi. Upon cooling to room temperature, the crude product was removed and worked up as usual. The product was found to contain 0.56% of phosphine as determined by the ceric sulfate titration method, 32.92% chlorine and 31 as the hydroxy number.

TABLE I

| Time Hours | Water Collected ml. |
|---|---|
| 0 | 0 |
| 2.0 | Began to condense |
| 5.25 | 5 |
| 9.25 | 23.5 (theo. 24) |

What is claimed is:

1. A process of producing a tertiary haloalkylphosphine oxide comprising reacting under acidic conditions a tertiary phosphine having at least one hydroxyalkyl group attached to the phosphorus atom, with a hydrogen halide selected from the class consisting of hydrogen chloride and hydrogen bromide whereby the hydroxy is replaced with halide to form the corresponding tertiary haloalkylphosphine and elimination of water which under the said acidic conditions reacts with the tertiary haloalkylphosphine to give the tertiary haloalkylphosphine oxide aforesaid.

2. The process of claim 1 wherein the hydrogen halide is hydrogen chloride.
3. The process of claim 1 wherein the reaction is carried out at a temperature of from about 100° C. to about 200° C.
4. The process of claim 1 wherein water is removed during the reaction, but retaining sufficient water to form the phosphine oxide.
5. The process of claim 1 wherein the acidic conditions are provided by an excess of the hydrogen halide.
6. A process of producing a tertiary haloalkylphosphine oxide of the formula:

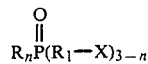

wherein R is a hydrocarbon radical, X is chlorine or bromine, R₁ is an alkylene radical and n is 0, 1 or 2, comprising reacting at a temperature of from about 100° C. to about 200° C. under acidic conditions a tertiary hydroxyalkyl phosphine of the formula:

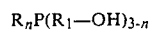

with hydrogen halide; wherein the halide is chloride or bromide whereby OH is replaced by X and one molecule of water is eliminated for each OH replaced by X to form R$_n$P(R₁—X)$_{3-n}$ which reacts with the water under the said acidic conditions to form the tertiary haloalkylphosphine aforesaid.

7. The process of claim 6 wherein the tertiary haloalkylphosphine oxide produced is

8. The process according to claim 6 wherein the tertiary haloalkylphosphine oxide produced is

9. The process of claim 6 wherein the tertiary haloalkylphosphine oxide produced is

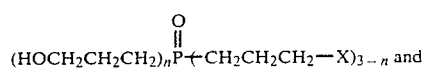

wherein n is 1 to 2.

10. The process of claim 6 wherein the tertiary haloalkylphosphine oxide produced is

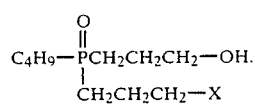

* * * * *